US00PP35043P2

(12) United States Plant Patent
van den Hoogen

(10) Patent No.: US PP35,043 P2
(45) Date of Patent: Mar. 14, 2023

(54) HYPERICUM PLANT NAMED 'ALLHYTIA'

(50) Latin Name: ***Hypericum androseamum* L.**
Varietal Denomination: Allhytia

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 13 days.

(21) Appl. No.: 17/889,222

(22) Filed: Aug. 16, 2022

(51) Int. Cl.
*A01H 5/08* (2018.01)
*A01H 6/00* (2018.01)

(52) U.S. Cl.
USPC ..... Plt./442

(58) Field of Classification Search
USPC ..... Plt./442, 226
CPC ... A01H 5/08; A01H 5/02; A01H 5/00; A01H 6/00
See application file for complete search history.

(56) References Cited

PUBLICATIONS

Fifty Flowers Peaches and Cream Hypericum Berries, retrieved on Sep. 7, 2022 at https://fiftyflowers.com/products/peaches-and-cream-hypericum-berries, 3 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Hypericum* plant named 'Allhytia', characterized by its upright plant habit; vigorous growth habit; dark green-colored leaves; freely flowering habit and high fruit density; large glossy pink and white-colored fruits; and suitability as a cut flower plant.

2 Drawing Sheets

Figure 1:
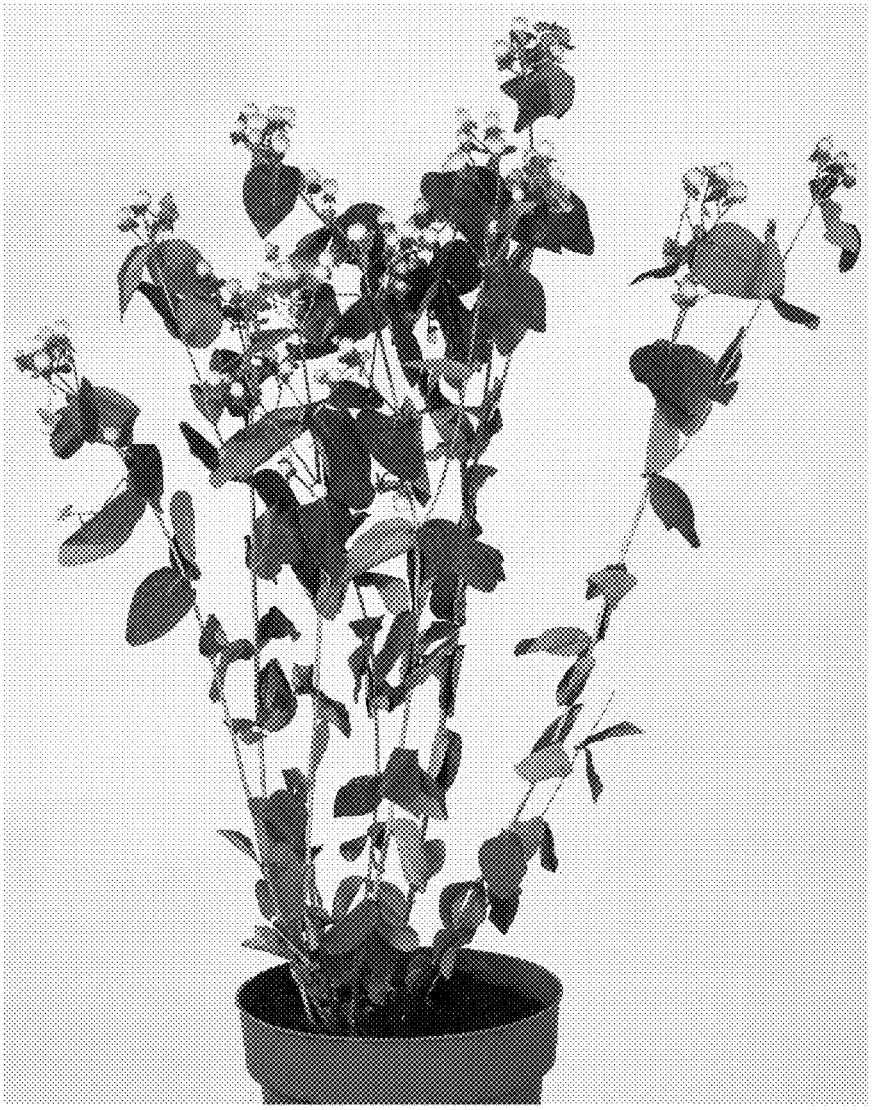

Botanical designation: *Hypericum androseamum* L.
Cultivar denomination: 'ALLHYTIA'.

STATEMENT REGARDING PRIOR DISCLOSURES BY INVENTOR/APPLICANT

An European Community Plant Breeder's Rights application for the instant plant was filed by the Assignee, Allplants Holding B.V. of Cuijk, The Netherlands on Nov. 19, 2021, application number 2021/2987. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hypericum* plant, botanically known as *Hypericum androseamum* L., typically grown as cut flower and hereinafter referred to by the name 'Allhytia'.

The new *Hypericum* plant is a product of a planned breeding program conducted by the Inventor in Cuijk, The Netherlands. The objective of the breeding program is to create new *Hypericum* plants with numerous attractive fruits.

The new *Hypericum* plant originated from an open-pollination in August, 2015 in Cuijk, The Netherlands of a proprietary selection of *Hypericum androseamum* L. identified as code number T13-18, not patented, as the female, or seed parent with an unknown selection of *Hypericum androseamum* L. as the male, or pollen, parent. The new *Hypericum* plant was discovered and selected by the Inventor as a single flowering plant from within the progeny of the stated open-pollination in a controlled outdoor nursery environment in Cuijk, The Netherlands in September, 2016.

Asexual reproduction of the new *Hypericum* plant by vegetative cuttings in a controlled outdoor nursery environment in Cuijk, The Netherlands since October, 2016 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allhytia'. These characteristics in combination distinguish 'Allhytia' as a new and distinct *Hypericum* plant:

1. Upright plant habit.
2. Vigorous growth habit.
3. Dark green-colored leaves.

4. Freely flowering habit and high fruit density.
5. Large glossy pink and white-colored fruits.
6. Suitable as a cut flower plant.

Plants of the new *Hypericum* differ primarily from plants of the female parent selection in fruit color as plants of the new *Hypericum* have pink and white-colored fruits whereas fruits of plants of the female parent selection are dark red to brown in color.

Plants of the new *Hypericum* can be compared to plants of the *Hypericum hybrida* 'Allloco', not patented. In side-by-side comparisons plants of the new *Hypericum* differ primarily from plants of 'Allloco' in the following characteristics:

1. Plants of the new *Hypericum* and 'Allloco' differ in fruit color as plants of the new *Hypericum* have pink and white-colored fruits whereas fruits of plants of 'Allloco' are lighter pink in color.
2. Fruits of plants of the new *Hypericum* are more rounded in shape than fruits of plants of 'Allloco'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet (FIG. 1) is a side perspective view of a typical plant of 'Allhytia' when fruiting grown in a container.

Figure 2:
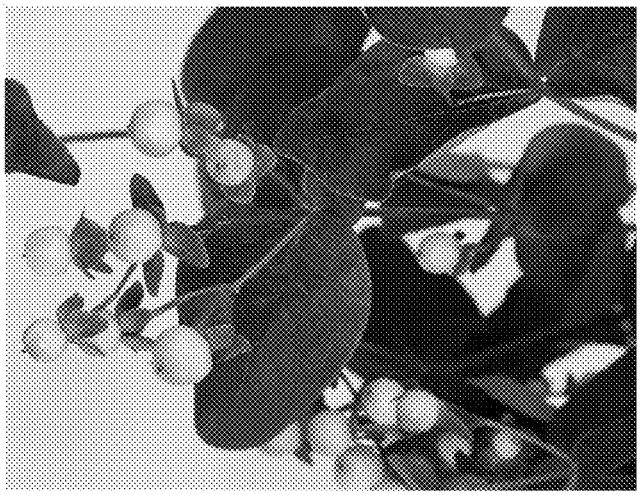

The photograph at the left of the second sheet (FIG. 2) is a close-up view of typical fruiting stems of 'Allhytia'.

Figure 3:
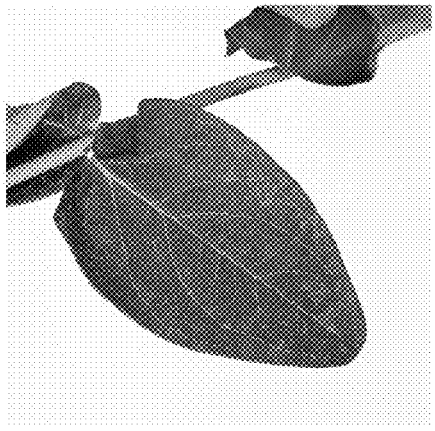

The photograph at the center of the second sheet (FIG. 3) is a close-up view of a typical stem and leaves of 'Allhytia'.

Figure 4:
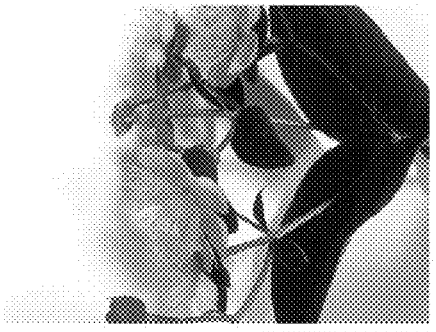

The photograph at the right of the second sheet (FIG. 4) is a close-up view of typical flowers and developing fruits of 'Allhytia'.

DETAILED BOTANICAL DESCRIPTION

Plants used for the aforementioned photographs and following description were grown in September in containers and ground beds in an outdoor nursery in Timau, Kenya and under cultural practices typical of commercial *Hypericum* production. During the production of the plants, day temperatures ranged from 23° C. to 28° C. and night temperatures ranged from 7° C. to 12° C. Plants were one year old when the photographs and description were taken. In the following description, color references are made to The Royal Horticultural Society Colour Chart, 2015 Edition, except where general terms of ordinary dictionary significance are used.

Botanical classification: *Hypericum androseamum* L. 'Allhytia'.

Parentage:

*Female, or seed, parent*.—Proprietary selection of *Hypericum androseamum* L. identified as code number T13-18, not patented.

*Male, or pollen, parent*.—Unknown selection of *Hypericum androseamum* L., not patented.

Propagation:

*Type cutting*.—Vegetative cuttings.

*Time to initiate roots, summer*.—About three weeks at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub; upright plant habit; overall plant shape, narrow inverted triangle; vigorous growth habit and moderate to high growth rate.

*Branching habit*.—When pinched, about three to seven basal branches develop per plant.

*Plant height*.—About 71 cm.

*Plant width* (*spread*).—About 40.3 cm.

*Lateral branch description*.—Length: About 41.8 cm. Diameter: About 4 mm. Internode length: About 5.7 cm. Strength: Moderately strong to strong. Texture and luster: Smooth, glabrous; slightly glossy. Color, developing: Close to 147D, mottled and blushed with close to N199C. Color, fully developed: Close to 200A to 200C.

Leaf description:

*Arrangement*.—Opposite, simple; sessile; about 16 leaves (eight pairs) develop per lateral branch.

*Length*.—About 6.9 cm.

*Width*.—About 4.6 cm.

*Shape*.—Ovate.

*Apex*.—Mostly obtuse to minutely retuse.

*Base*.—Cordate.

*Margin*.—Entire.

*Texture and luster, upper surface*.—Smooth, glabrous; slightly glossy.

*Texture and luster, lower surface*.—Slightly rugose, glabrous; matte.

*Venation pattern*.—Pinnate.

*Color*.—Developing leaves, upper surface: Close to NN137C. Developing leaves, lower surface: Close to a blend of N138B and 191A. Fully expanded leaves, upper surface: Close to a blend of NN137A and 147A to slightly darker than NN137A; venation, close to 145A. Fully expanded leaves, lower surface: Close to 191A; venation, close to 152D.

Flower description:

*Flower type, arrangement and flowering habit*.—Single rotate flowers arranged in terminal and axillary compound cymes; freely flowering habit with about nine flowers per cyme and about 15 flowers per lateral branch; flowers face mostly upright.

*Fragrance*.—None detected.

*Natural flowering season*.—Plants flower continuously June to early September in The Netherlands; plants begin flowering about ten months after planting.

*Flower longevity*.—Flowers last about three days on the plant; flowers not persistent.

*Fruit longevity* (*postproduction*).—About 30 days.

*Flower buds*.—Length: About 8 mm. Diameter: About 6 mm. Shape: Broadly elliptic. Color: Close to 12A.

*Inflorescence height*.—About 6.9 cm.

*Inflorescence diameter*.—About 7.7 cm.

*Flower diameter*.—About 2.7 cm.

*Flower depth* (*height*).—About 1.5 cm.

*Petals*.—Quantity and arrangement: Five in a single whorl. Length: About 1.2 cm. Width: About 1 cm. Shape: Broadly elliptic, concave; horizontal to slightly reflexed. Apex: Acute, unequal. Base: Attenuate. Margin: Entire. Texture and luster, upper surface: Smooth, glabrous; matte. Texture and luster, lower surface: Smooth, glabrous; moderately glossy. Color: When opening and fully opened, upper surface: Close to 12A; color becoming closer to 13A with subsequent development. When opening and fully opened, lower surface: Close to 12A; color becoming closer to 13A with subsequent development.

*Sepals*.—Quantity and arrangement: Five in a single whorl. Length: About 1 cm. Width: About 8 mm. Shape: Broadly ovate; horizontal to moderately reflexed. Apex: Acute to obtuse. Base: Broadly cuneate. Margin: Entire. Texture and luster, upper and lower surfaces: Smooth, glabrous; matte. Color: When opening, upper surface: Close to 141A. When opening, lower surface: Close to 137C. Fully opened, upper surface: Close to between 136A and 141A. Fully opened, lower surface: Close to 137C.

*Peduncles*.—Length: About 2.7 cm. Diameter: About 1.75 mm. Texture: Smooth, glabrous. Strength: Moderately strong. Aspect: Main peduncles, erect; lateral peduncles, about 50° from main peduncles axis. Color: Close to 144A.

*Pedicels*.—Length: About 1.5 cm. Diameter: About 1.5 mm. Texture: Smooth, glabrous. Strength: Moderately strong. Aspect: Main pedicels, erect; lateral pedicels, about 30° from main peduncle axis. Color: Close to N144A.

*Reproductive organs*.—Stamens: Quantity per flower: About 80. Filament length: About 1.3 cm. Filament color: Close to 12A. Anther length: About 0.5 mm. Anther shape: Broadly oval; dorsifixed. Anther color: Close to 12A and 23A. Pollen amount: Scarce. Pollen color: Close to 11A. Pistils: Quantity per flower: Single pistil with three stigmas. Pistil length: About 4 mm. Stigma shape: Club-shaped. Stigma color: Close to 12A. Style length: About 4 mm. Style color: Close to 4A and 2C. Ovary color: Close to 4A.

*Fruits*.—Quantity per lateral branch: About 15. Length: About 1.1 cm. Diameter: About 1.3 cm. Shape: Roughly spherical. Texture and luster: Smooth, glabrous; glossy. Color: Close to 48C, 50B and 50C; proximally, fading to close to 155C and 157D.

*Seeds*.—Quantity per fruit: More than 100. Length: About 0.9 mm. Diameter: About 0.5 mm. Color: Close to 200A.

Pathogen & pest resistance: To date, plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allhytia' as illustrated and described.

* * * * *